(12) United States Patent
Karapasha

(10) Patent No.: US 9,078,726 B2
(45) Date of Patent: *Jul. 14, 2015

(54) PESSARY DEVICE WITH LONGITUDINAL FLEXIBILITY

(75) Inventor: Nancy Karapasha, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 131 days.

This patent is subject to a terminal disclaimer.

(21) Appl. No.: 13/084,032

(22) Filed: Apr. 11, 2011

(65) Prior Publication Data
US 2012/0259161 A1 Oct. 11, 2012

(51) Int. Cl.
*A61F 2/00* (2006.01)
*A61F 5/48* (2006.01)
*A61F 6/08* (2006.01)

(52) U.S. Cl.
CPC ................ *A61F 2/0009* (2013.01); *A61F 5/48* (2013.01); *A61F 6/08* (2013.01)

(58) Field of Classification Search
CPC .......... A61F 2/005; A61F 2/0009; A61F 6/08
USPC ......... 128/834–836, 830, 837, 838, 884, 885, 128/DIG. 25; 600/29, 30, 37
See application file for complete search history.

(56) References Cited

U.S. PATENT DOCUMENTS

| | | | |
|---|---|---|---|
| 395,005 A | 12/1888 | Sharp | |
| 404,019 A | 5/1889 | Sperry | |
| 525,785 A | 9/1894 | Hurdle | |
| 748,650 A | 1/1904 | Priest | |
| 1,222,825 A | 4/1917 | Walter | |
| 1,604,511 A | 10/1926 | Hill | |
| 2,049,270 A | 7/1936 | Munro | |
| 2,092,427 A | 9/1937 | Ross | |
| 2,457,349 A | 12/1948 | Clark | |
| 3,452,752 A | 7/1969 | Crescenzo | |
| 4,019,498 A | 4/1977 | Hawtrey et al. | |
| 4,307,716 A | 12/1981 | Davis | |
| 5,554,092 A * | 9/1996 | Harpstead et al. | 482/148 |
| 6,413,206 B2 | 7/2002 | Biswas | |
| 6,458,072 B1 * | 10/2002 | Zunker | 600/29 |
| 6,503,190 B1 | 1/2003 | Ulmsten et al. | |
| 6,739,340 B1 | 5/2004 | Jensen et al. | |
| 6,770,025 B2 | 8/2004 | Zunker | |
| 6,808,485 B2 | 10/2004 | Zunker | |
| 7,351,195 B2 | 4/2008 | Farrell | |
| 7,717,892 B2 | 5/2010 | Bartning et al. | |
| 7,771,344 B2 | 8/2010 | Ziv | |

(Continued)

FOREIGN PATENT DOCUMENTS

| | | |
|---|---|---|
| WO | WO-94/13223 A1 | 6/1994 |
| WO | WO-96/10965 A1 | 4/1996 |
| WO | WO-2008/063085 A1 | 5/2008 |

*Primary Examiner* — Charles A Marmor, II
*Assistant Examiner* — Carrie R Dorna
(74) *Attorney, Agent, or Firm* — Andres E. Velarde; Amanda T. Barry

(57) ABSTRACT

An intravaginal pessary device. The device has a top, a mid-section, and a bottom. The device has a sidewall that extends between the top and the bottom, and the top, the bottom, and the sidewall form an outer periphery defining a total area of the device. The top has a first width and the mid-section has a second width, and the first width is greater than the second width. In addition, the top has a first flexibility and the mid-section has a second flexibility, and the first flexibility is greater than the second flexibility.

5 Claims, 6 Drawing Sheets

(56) References Cited

U.S. PATENT DOCUMENTS

| | | |
|---|---|---|
| 2002/0120243 A1 | 8/2002 | Kraemer et al. |
| 2003/0149334 A1* | 8/2003 | Ulmsten et al. ................. 600/29 |
| 2005/0113781 A1 | 5/2005 | Forgeot et al. |
| 2005/0148995 A1 | 7/2005 | Shepard et al. |
| 2007/0244352 A1* | 10/2007 | Ziv ................................. 600/29 |
| 2008/0009814 A1 | 1/2008 | Bartning et al. |
| 2009/0095304 A1 | 4/2009 | Richardson et al. |
| 2009/0203959 A1 | 8/2009 | Ziv et al. |
| 2010/0145137 A1 | 6/2010 | Morgan |

\* cited by examiner

PESSARY DEVICE WITH LONGITUDINAL FLEXIBILITY

FIELD OF INVENTION

This application relates to pessary devices for relief of female incontinence. More particularly, the present invention relates to pessary devices with longitudinal flexibility.

BACKGROUND OF THE INVENTION

Urinary incontinence, in which the ordinary bodily muscle functions fail to prevent unintended leakage of urine, is a common malady among women, particularly older women. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. Many women wear sanitary napkins or diapers in order to deal with incontinence, and some women resort to surgical procedures.

Pessary devices are known to help relieve involuntary urination in a female. Such devices are designed for arrangement in the vagina for compressive action on and support of the bladder. Typical pessary devices are large in width during use, and may elastically expand, inflate, or unfold to provide compressive action within the vagina. Such pessary devices can be uncomfortable for a user and/or can require the user to activate or operate the device prior to or upon insertion of the pessary device into the vagina. This can result in an undesirable usage experience.

As such, there remains a need for a pessary device with improved comfort during use. There also remains a need for a pessary device that is small in size yet effective. In addition, there remains a need for a disposable pessary device that can be used daily.

SUMMARY OF THE INVENTION

An intravaginal pessary device, the device having a top, a mid-section, and a bottom is provided. The device has a sidewall that extends between the top and the bottom, and the top, the bottom, and the sidewall form an outer periphery defining a total area of the device. The top has a first width and the mid-section has a second width, and the first width is greater than the second width. In addition, the top has a first flexibility and the mid-section has a second flexibility, and the second flexibility is greater than the first flexibility.

Also provided is an intravaginal pessary device. The device has a top, a mid-section, a bottom, and a sidewall that extends between the top and the bottom. The top, the bottom, and the sidewall form an outer periphery defining a total area of the device. The bottom has a first width and the mid-section has a second width, and the first width is greater than the second width. The bottom has a first flexibility and the mid-section has a second flexibility, and the first flexibility is greater than the second flexibility.

Further provided is an intravaginal pessary device. The device has a top and a bottom, and a sidewall that extends between the top and the bottom. The top, the bottom, and the sidewall form an outer periphery defining a total area of the device. The device has a first region with a first width and a second region with a second width, and the first width is greater than the second width. The first region also has a first flexibility and the second region has a second flexibility, and the first flexibility is greater than the second flexibility.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1A:
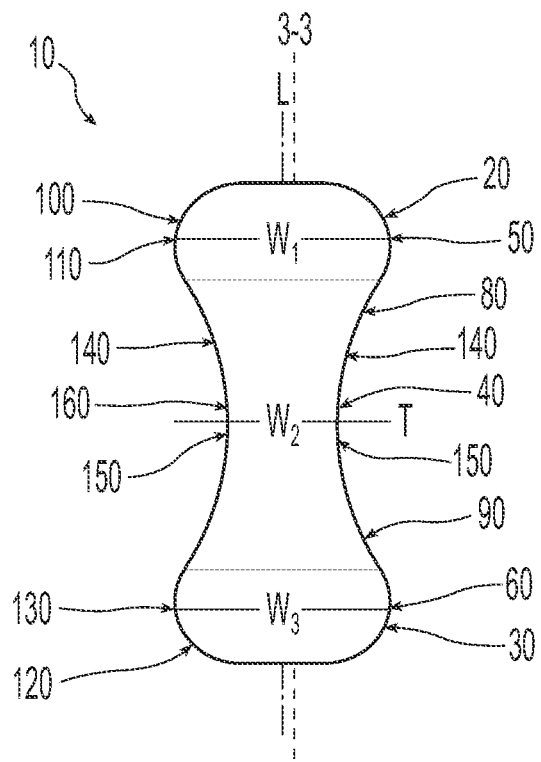
FIG. 1A is a side view of a pessary device.

The present invention is directed to pessary devices that are inserted into the female vagina to help control involuntary urinary incontinence. The pessary devices are non-expandable, small in size, and can provide improved comfort during use. The pessary devices can include a first portion having a first width that is adapted to extend between an anterior vaginal wall and a posterior vaginal wall of a user to provide pressure on the user's urethra through the vaginal wall. The first portion can include the maximum width of the pessary. The pessary device can also include a second portion having a second width provided distal from the first portion. The second portion can include the minimum width of the pessary device. The second portion can be more flexible than the first portion, and the first portion can be more resistant than the second portion under high stress conditions, such as, for example, when the user coughs. This can provide for a small and comfortable, yet effective, pessary device.

A woman with stress incontinence can experience involuntary loss of urine with increases in abdominal pressure, such as, for example, during exercise, coughing, sneezing, laughing, or valsalva maneuvers. This loss of urine is thought to occur because the muscles and connective tissue that support the bladder and/or urethra are weakened or injured and cannot fully support the bladder and/or urethra during stress incidents, leading to leaks. Physical changes due to childbirth, menopause, injury, surgery, and pelvic organ prolapse can often cause stress incontinence. Surprisingly, the pessary devices described herein can provide resistance sufficient to prevent leakage during increases in abdominal pressure while remaining flexible and small enough to provide comfort during wear.

As used herein, "applicator" refers to a device or implement that facilitates the insertion of the pessary device into an external orifice of a mammal. Exemplary applicators include telescoping, tube and plunger, and compact applicators.

The term "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

As used herein, the term "non-expandable" refers to devices that do not expand prior to or during use, such as, for example, devices that do not substantially increase in size or volume prior to or during use. For example, non-expandable devices have a diameter and/or volume that does not substantially increase. In contrast, "expandable" as used herein, refers to devices that do increase in size or volume prior to or during use, such as, for example, devices that increase in diameter and/or length, absorb fluid into a fibrous or absorbent gelling material structure, or otherwise change from a first size or volume to a second size or volume, such as, for example, by inflation, absorption, mechanically, user action, or by other means. Insubstantial changes to a non-expandable device as a result of any thermal expansion that could occur at body temperatures are not considered "expansion."

A "pessary device" or more particularly an "incontinence pessary device" as used herein refers to devices specifically designed, configured, and/or adapted for placement into a vagina in order to reduce the occurrence and/or severity of female urinary incontinence. A "pessary device" can include any type of substantially non-absorbent structure for the purpose of reducing urine leakage and/or supporting a prolapsed uterus and/or bladder. A pessary device does not include a menstrual tampon.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

Figure 1B:
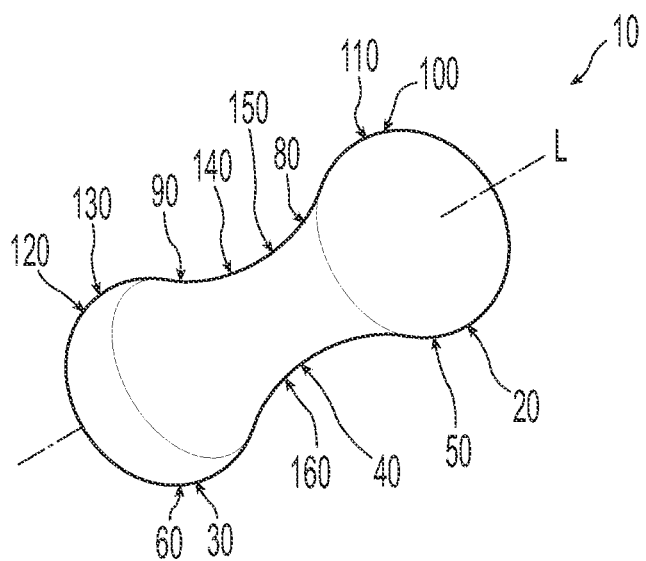
FIG. 1B is a perspective view of the pessary device of FIG. 1A.

An exemplary pessary device 10 is shown in FIGS. 1A and 1B. The pessary device 10 includes an upper portion 20, a lower portion 30, a middle portion 40, a pressure region 50 of the upper portion 20, a pressure region 60 of the lower portion 30, a maximum width $W_1$, a minimum width $W_2$, a slope 80 extending from the upper portion 20 to the middle portion 40, a slope 90 from the middle portion 40 to the lower portion 30, a longitudinal axis (L) and a transverse axis (T). As shown in FIGS. 1A and 1B, the pessary device 10 can have a top 100 that includes a convex portion 110, a base 120 that includes a convex portion 130, and sides 140 that include concave portions 150. The pessary device can be symmetric about the longitudinal axis, including for example, wherein the base is circular and symmetric about the longitudinal axis. The pessary device can include a third width $W_3$ that is greater than minimum width $W_2$, and convex portion 110 can be aligned with maximum width $W_1$ to provide pressure region 50, and convex portion 130 can be aligned with maximum width $W_1$ to provide pressure region 60. In addition, concave portion 150 can be aligned with minimum width $W_2$ to form flexile region 160.

Figure 2A:
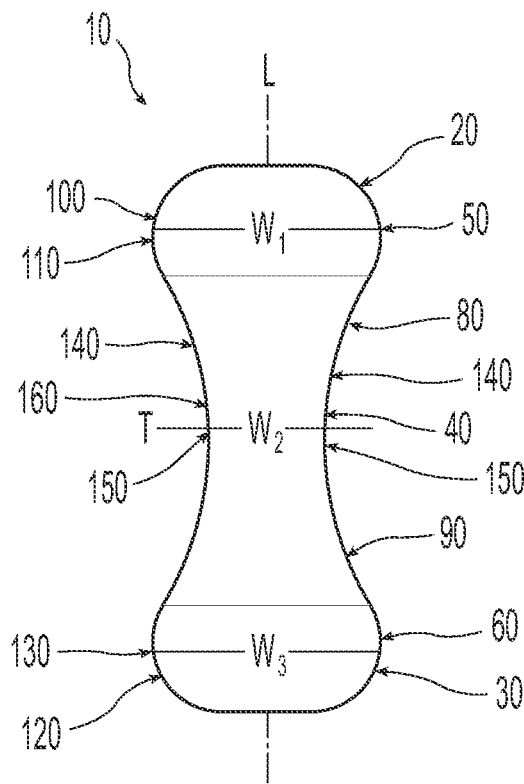
FIG. 2A is a side view of a pessary device.
Figure 2B:
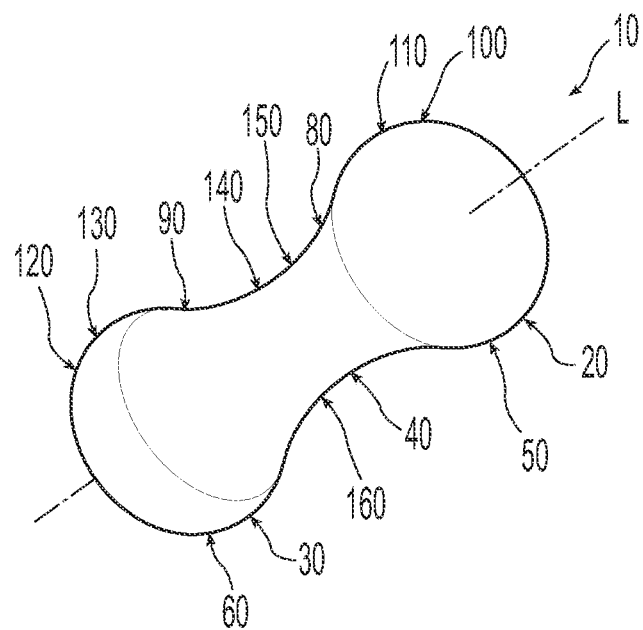
FIG. 2B is a perspective view of the pessary device of FIG. 2B.

FIGS. 2A and 2B show a pessary device 10. The pessary device 10 includes an upper portion 20, a lower portion 30, a middle portion 40, a pressure region 50 of the upper portion 20, a pressure region 60 of the lower portion 30, a maximum width $W_1$, a minimum width $W_2$, a slope 80 extending from the upper portion 20 to the middle portion 40, a slope 90 from the middle portion 40 to the lower portion 30, a longitudinal axis (L) and a transverse axis (T). As shown in FIGS. 2A and 2B, the pessary device 10 can have a top 100 that includes a convex portion 110, a base 120 that includes a convex portion 130, and sides 140 that include concave portions 150. The pessary device 10 can also include a flexile region 160. The pessary device shown in FIGS. 2A and 2B has an upper slope 80 that is greater than the upper slope 80 of the pessary device shown in FIGS. 1A and 1B. In addition, the pessary device shown in FIGS. 2A and 2B has a lower slope 90 that is greater than the lower slope 90 of the pessary device shown in FIGS. 2A and 2B.

Figure 3:
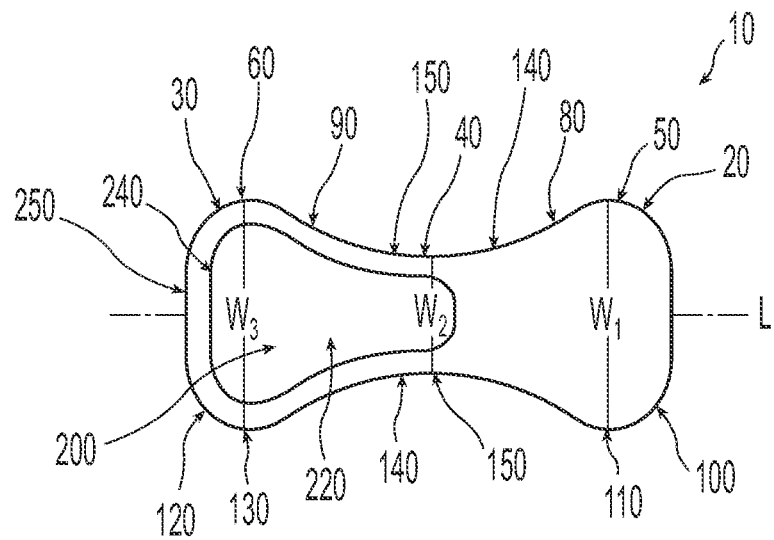
FIG. 3 is a cross-section view of a pessary device.

FIG. 3 shows a pessary device 10 taken along line 3-3 of FIG. 1. The pessary device 10 includes an upper portion 20, a lower portion 30, a middle portion 40, a pressure region 50 of the upper portion 20, a pressure region 60 of the lower portion 30, a maximum width $W_1$, a minimum width $W_2$, a slope 80 extending from the upper portion 20 to the middle portion 40, a slope 90 from the middle portion 40 to the lower portion 30, a longitudinal axis (L) and a transverse axis (T). As shown in FIG. 3, the pessary device 10 can have a top 100 that includes a convex portion 110, a base 120 that includes a convex portion 130, and sides 140 that include concave portions 150. As shown in FIG. 3, the pessary device 10 can have outer wall 250 and an interior 200 defined by inner walls 240 that is hollow in region 220. The hollow region 220 can be provided at one or both ends. In addition, the pessary device 10 can have a portion of the interior 200 that is solid.

Figure 4:
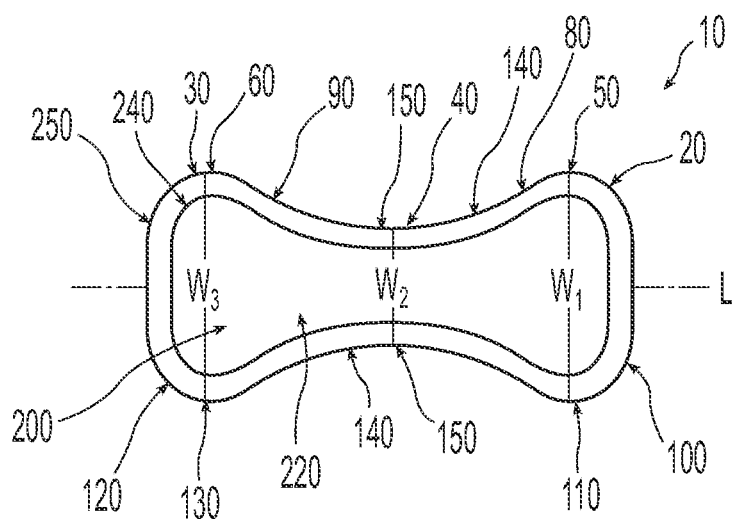
FIG. 4 is a cross-section view of a pessary device.

FIG. 4 shows a pessary device 10. The pessary device 10 includes an upper portion 20, a lower portion 30, a middle portion 40, a pressure region 50 of the upper portion 20, a pressure region 60 of the lower portion 30, a maximum width $W_1$, a minimum width $W_2$, a slope 80 extending from the upper portion 20 to the middle portion 40, a slope 90 from the middle portion 40 to the lower portion 30, and a longitudinal axis (L). As shown in FIG. 4, the pessary device 10 can have a top 100 that includes a convex portion 110, a base 120 that includes a convex portion 130, and sides 140 that include concave portions 150. As shown in FIG. 4, the pessary device 10 can have an interior 200 that is hollow. The pessary device has inner walls 240 that define interior 200 and hollow region 220. In addition, the inner walls 240 can have the same or a similar profile as the outer walls 250.

Figure 5:
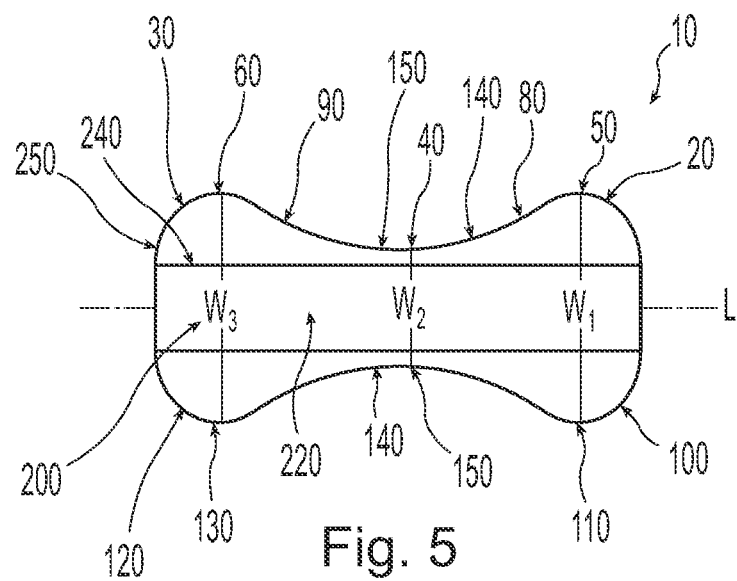
FIG. 5 is a cross-section view of a pessary device.

FIG. 5 shows a pessary device 10. The pessary device 10 includes an upper portion 20, a lower portion 30, a middle portion 40, a pressure region 50 of the upper portion 20, a pressure region 60 of the lower portion 30, a maximum width $W_1$, a minimum width $W_2$, a slope 80 extending from the upper portion 20 to the middle portion 40, a slope 90 from the middle portion 40 to the lower portion 30, and a longitudinal axis (L). As shown in FIG. 5, the pessary device 10 can have a top 100 that includes a convex portion 110, a base 120 that includes a convex portion 130, and sides 140 that include concave portions 150. As shown in FIG. 5, the pessary device 10 has an interior 200 that is hollow. The pessary device has inner walls 240 that define interior 200 and hollow region 220. The hollow region 220 can have a first profile defined by inner walls 240 and a different profile defined by outer walls 250, such as, for example, where the hollow region 220 is in the form of a tube.

Figure 6:
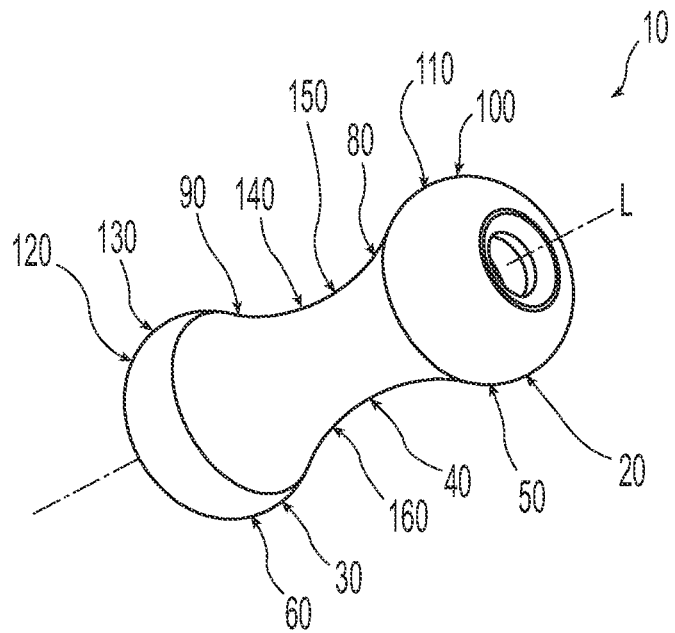
FIG. 6 is a perspective view of a pessary device.

FIG. 6 shows a pessary device 10. The pessary device 10 includes an upper portion 20, a lower portion 30, a middle portion 40, a pressure region 50 of the upper portion 20, a pressure region 60 of the lower portion 30, a slope 80 extending from the upper portion 20 to the middle portion 40, a slope 90 from the middle portion 40 to the lower portion 30, and a longitudinal axis (L). As shown in FIG. 6, the pessary device 10 can have a top 100 that includes a convex portion 110, a base 120 that includes a convex portion 130, and sides 140 that include concave portions 150. As shown in FIG. 6, the pessary device 10 can have an interior 200 that is hollow. In addition, as shown in FIG. 6, the pessary device 10 can have an opening on one or more of top 100 and/or on base 120.

Figure 7:
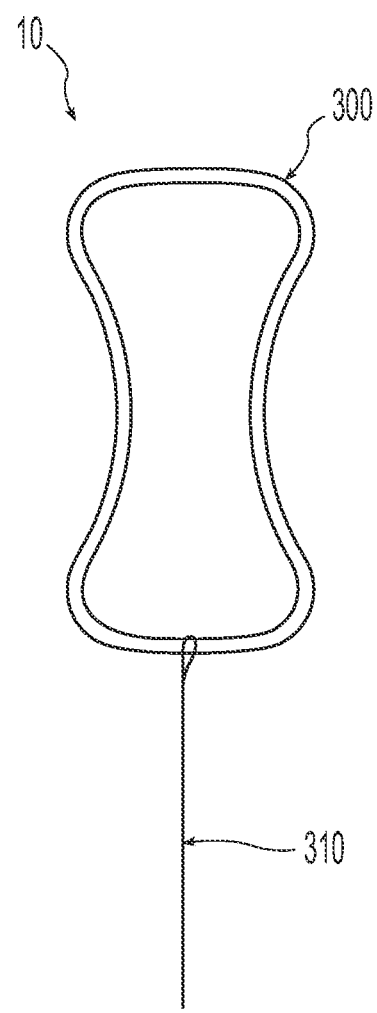
FIG. 7 is a side view of a pessary device.

The pessary device 10 can include an overwrap 300 and/or a withdrawal member 310, such as, for example, as shown in FIG. 7. In addition, FIG. 7 shows that withdrawal member 310 can be attached to overwrap 300.

Figure 8:
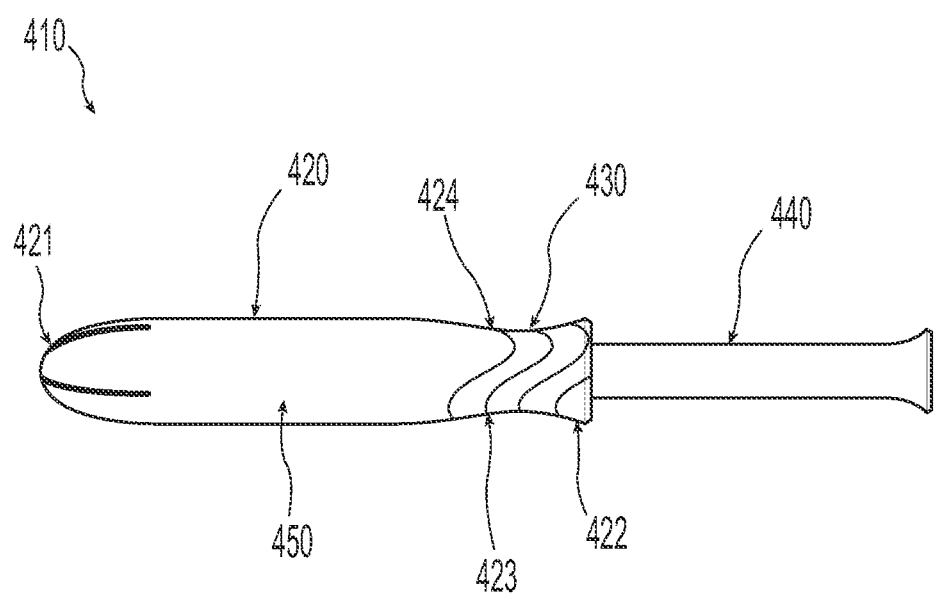
FIG. 8 is a side view of a pessary applicator, housing the pessary of FIG. 1.

The pessary device can be inserted in any suitable manner, such as, for example, using an applicator. FIG. 8 shows an applicator 410 that includes an insertion member 420 and a plunger 440. The insertion member 420 has an insertion end 421 and a withdrawal end 422 opposite the insertion end 421. The insertion member 420 also can include a barrel region 450 adapted to contain the pessary device, and a grip region 430 that can be an indentation region 424 provided opposite the insertion end 421, such as, e.g., proximal to the withdrawal end 422. The grip region 430 can include one or more grip elements 423.

Generally, the pessary device does not change in size during the usage experience, that is, the pessary device is the same size and diameter prior to insertion by the user as well as during use and removal. For example, the pessary device is not expandable or inflatable from its original size and the pessary device is not compressed for insertion into the user's body, nor is the pessary device compressed for withdrawal from the user's body. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can have a first width and a second width, wherein the first width is greater than the second width. The first width can correspond to the top, the bottom, or both, and the second width can correspond to the mid-section. In addition, the region having the first width can have a first resistance to pressure and the region having the second width can have a second resistance to pressure, the first resistance being greater than the second resistance. For example, the region having the first resistance can have a first flexibility that is greater than a flexibility of the region having the second resistance.

The region having the first width can be convex and can extend between the anterior vaginal wall and the posterior vaginal wall of a consumer to provide pressure on the urethra through the vaginal wall. In addition, the pessary device can have a second convex portion having an increased width compared to the second width that can provide pressure on the urethra through the vaginal wall at a point distal from the first convex portion. The first convex portion and the second convex portion can be separated by any suitable distance, such as, for example, by at least about 5 mm, at least about 10 mm, at least about 15 mm, at least about 20 mm, at least about 25 mm, at least about 30 mm, at least about 35 mm, at least about 40 mm, at least about 45 mm, at least about 50 mm, or any other suitable distance.

The pessary device can have any suitable number of convex portions, including for example, four or fewer convex portions, three or fewer convex portions, two or fewer convex portions, one convex portion, or any other suitable number of convex portions.

The region having the first width can be any suitable shape, such as, for example, a convex shape that provides pressure to the vaginal wall, such as, for example, a lobe or other protuberance. The region having the first width can have a substantially circular cross-section. The pessary device can also include a region having the second width that can provide flexibility to the pessary device, such as, for example, by allowing bending or movement at the region. The region having the second width can be any suitable shape, such as, for example, concave, indented, or the like, and can have suitable cross-section, such as, for example, a substantially circular cross-section.

The region having the first width can have a first flexibility and the region having the second width can have a second flexibility, the first flexibility being greater than the second flexibility. Flexibility can be measured in any suitable manner, such as, for example, by the Gardner Impact Test using a Gardner Variable Impact Tester in accordance with ASTM-D 5420-04.

The pessary device can provide resistance to force when placed inside a woman's vagina. For example, when the pessary device is inserted into the vagina, increases in abdominal pressure can act as a force on the pessary device through the vaginal wall. When the pessary device is disposed in the vagina lengthwise, that is, with the top of the pessary device positioned toward the cervix, the bottom of the pessary device positioned toward the introitus, and the length of the pessary device generally aligned with the length of the vagina, increases in abdominal pressure can act on the side of the pessary device, perpendicular to the length of the pessary device. Of course, increases in abdominal pressure can act on other regions of the pessary device, in addition or alternatively to acting on the side of the pessary device, including for example, when the pessary device is inserted into the vagina in an orientation other than lengthwise.

Despite its small size, the pessary device can provide a resistance to force of greater than about 10 psi, greater than about 15 psi, greater than about 20 psi, or greater than about 25 psi under about 2 newtons of force. For example, in certain embodiments, the pessary device can provide a resistance to force of greater than about 20 psi under about 2 newtons of force and greater than about 25 psi under about 3 newtons of force. The pessary device also can resist compression under pressure. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force.

The pessary devices can provide a varied resistance to force along the longitudinal axis of the pessary device. For example, the pessary device can provide a resistance to force that is greater at the maximum diameter regions and smaller at the minimum diameter regions. In addition, the pessary device can compress differently along the longitudinal axis at different regions. For example, when force is applied to the side of the pessary, the minimum diameter region can compress at least about 5% more than the maximum diameter region under the same amount of pressure (for example, under about 200 g/m2 of force), at least about 10% more than the maximum diameter region under the same amount of pressure, at least about 15% more than the maximum diameter region under the same amount of pressure, at least about 20% more than the maximum diameter region under the same amount of pressure, or at least 25% more than the maximum diameter region under the same amount of pressure. Any suitable amount of force can be applied, such as, for example, from about 200 g/m2 of force to about 1500 g/m2 of force, from about 200 g/m2 of force to about 1400 g/m2 of force, from about 300 g/m2 of force to about 1200 g/m2 of force, or from about 400 g/m2 of force to about 800 g/m2 of force.

The amount of resistance to force and the amount of compression under force provided by the pessary device as a whole or provided by the different regions of the pessary device can be measured in any suitable manner. For example, one suitable method employs a Universal Constant Rate Elongation/Tensile Tester with computer interface (MTS, Eden Prairie, Minn.). The method measures the force required to compress the pessary device resting on its side at 0.8 mm at a rate of 20 mm per min. For this method, the load probe tip is 5 mm in diameter and the tip is semi-spherical in shape. In addition, the resting fixture is a cylindrical steel plate 152 mm in diameter and 13 mm thick. The pessary device is placed on the steel table and the crosshead moves at 20 mm/min. When a force of 2 grams is exhibited on the pessary device, the crosshead automatically zeroes out and moves an additional 0.8 mm. The probe cycles back, and data is acquired at a rate of 100 Hz. This method measures the peak force in grams versus the amount of compression in mm. For pessary devices having varying diameters or widths, such as, for example, pessary devices having a maximum diameter or width and a minimum diameter or width, resistance to force at the different regions can be measured using this method. For example, for a pessary device as shown in FIGS. 1A and 1B, resistance to force at the maximum width regions $W_1$ and $W_3$ can be measured using a steel plate that is larger in size than the pessary device as the resting fixture. Resistance to force at the minimum diameter region $W_2$ can be measured using a single rod that contacts the minimum diameter region but not the maximum diameter regions.

Generally, the pressure region can be resistant such that the pressure region can provide pressure to the vaginal wall. The pressure region provides resistance under high stress pressures typical of the human vagina, such as, for example, by providing a maximum pressure to the urethra through the vaginal wall greater than about 5 psi, such as, for example, greater than about 10 psi, greater than about 15 psi, greater than about 20 psi, or greater than about 25 psi. In addition, the pressure region can provide a maximum urethral closure of greater than about 1.0 mm, such as, for example, greater than about 1.1 mm, greater than about 1.2 mm, greater than about 1.3 mm, greater than about 1.4 mm, such as, for example, greater than about 1.5 mm, greater than about 1.6 mm, greater than about 1.7 mm, greater than about 1.8 mm, or greater than about 1.9 mm. In addition, or alternatively, the pressure region can compress less than about 1 mm when measured under 0.5 psi when the force is applied from one side of the pressure region to the opposite side of the pressure region at the region of maximum width in the direction perpendicular to the longitudinal axis.

Maximum pressure to the urethra and maximum urethral closure can be measured using any suitable method, such as, for example, by using the computational model described in U.S. Patent Appln. No. 2007/0027667. For example, a computation model simulating the human internal pelvic environment can be used. In certain embodiments, thirteen nodes on the urethra in the simulation that are both on the back wall toward the vagina and in the middle of the body on the sagittal plane can be chosen. The points should be spread even along the length of the urethra with the first point at the bottom edge of the urethra and the last point at the bladder neck. Node vs. time vs. Von Mises stress should be obtained using a suitable software program, such as, for example, LS-Prepost, for all chosen nodes. The data columns are then matched to determine the y position vs. time vs. Von Mises stress. Generally, only the data that is at the simulation end point should be selected and y-position vs. Von Mises is then plotted.

The flexile region, on the other hand, is more flexible than and provides less resistance than the pressure region. Addition of the flexile region can allow the pessary device to flex in the longitudinal direction as well at the lateral direction. For example, the pessary device can compress more than about 1 cm when measured under 0.5 psi when the force is applied from the top to the base along the longitudinal axis. In addition, or alternatively, the flexile region can provide a bending region that facilitates the pessary device bending from side to side.

The pessary device can be a unitary construction. For example, the pessary device can include a continuous outer shell that defines the entire exterior surface of the pessary device. The outer shell can be smooth or textured. The outer shell may be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. In certain embodiments, the pessary device can include an opening in the top and/or base and the outer shell is not permeable to fluid such that fluid cannot enter the device except through the opening in the top and/or base.

Suitable pessary devices can be solid or can have a hollow interior. For hollow devices, the pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 1 mm, such as for example, about 2 mm, about 3 mm, about 4 mm, about 5 mm, or greater. The wall thickness can be constant or varied along the length of the pessary device and/or around the circumference of the pessary device.

The pessary device can have any suitable shape having a varied width along the longitudinal axis, such as, for example, a shape having a varied width that is symmetrical with respect to the longitudinal axis, such as, for example, a teardrop, an apple, a pear, an hourglass, a waisted cylinder, a figure-8 shape, a peanut shape, a heart-shape, a light bulb shape, a bottle shape, a vase shape, or any other suitable shape. In addition, the shape can have a varied width and can be symmetrical with respect to both the longitudinal and lateral axis, such as, for example, an hourglass, a waisted cylinder, a figure-8 shape, a peanut shape, or any other suitable shape. Alternatively, the pessary device can have an asymmetrical shape, such as, for example, a B-shape or a P-shape. The pessary device can be symmetrical at one region and asymmetrical at another region, such as, for example, where the pessary device has a symmetrical pressure region and an asymmetrical flexile region. Generally, the pessary device can have a varying width that can provide varying pressure along the user's urethra. For example, the pessary device can have a convex portion that can correspond to the pressure region. In addition, the pessary device can have a minimum width region that can be a concave region. The concave region can correspond to the flexile region.

The pessary device can be hourglass shaped. For example, as shown in FIGS. 1-2, the pessary device can have upper and lower portions joined together by a waistline portion, with the upper and lower portions having widths that are both greater than a width of the waistline portion such that the pessary device has a generally hourglass configuration. In this configuration, the upper portion of the pessary device can have a top and the lower portion of the pessary device can have a base, and the pessary device can have sloping upper and lower wall sections joining the top and the base with the waistline portion. In addition, the waistline portion can include the minimum width of the pessary device. The upper and lower portions can have generally coequal maximum widths, or the upper and lower portions can have different maximum widths, such as, for example, where the upper portion has a maximum width greater than the lower portion or where the lower portion has a maximum width greater than the upper portion.

Generally, the pessary device includes at least one maximum width and at least one minimum width, where the minimum width is smaller than the maximum width. The pessary device can include a first portion having a maximum width, a second portion having a maximum width, and a third portion that has a minimum width. The maximum width of the first portion and the maximum width of the second portion can be separated by a distance that is greater than about 10% of the length of the pessary device, such as, for example, by a distance greater than about 5 mm, greater than about 10 mm, greater than about 15 mm, greater than about 20 mm, greater than about 25 mm, greater than about 30 mm, greater than about 35 mm, greater than about 40 mm, greater than about 45 mm, or more. In certain embodiments, the pessary device provides pressure at mid-urethra, the bladder neck, or both. In addition, in certain embodiments, the pessary device provides higher pressure at the mid-urethra, the bladder neck, or both and provides lower pressure at the area between the mid-urethra and the bladder neck. For example, the pressure region can provide pressure at levels about 25% higher than the pressure provided by the flexile region, such as, for example, at levels about 30% higher, about 35% higher, about 40% higher, about 45% higher, about 50% higher, about 55% higher, about 60% higher, or more.

The pessary device can have a slope from the maximum width to the minimum width. Any suitable slope can be used, including for example, about 0.25 mm, about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, or more, such as, for example, a slope from about 0.25 mm to about 5 mm, or a slope from about 0.5 mm to about 4 mm, or any other suitable range.

Suitable pessary devices are typically smaller in size than conventional pessary devices. For example, the pessary devices have a maximum width, a length, and/or a volume that is smaller or less than that of conventional pessary devices.

The pessary devices can have any suitable maximum width, such as, for example, a maximum width of less than 35 mm, such as, for example, less than 34 mm, less than 33 mm, less than 32 mm, less than 31 mm, less than 30 mm, less than 29 mm, less than 28 mm, less than 27 mm, less than 26 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, or less than 10 mm, including, for example, a maximum width of from about 10 mm to about 35 mm, from about 10 mm to about 25 mm, from about 13 mm to about 25 mm, or from about 15 mm to about 22 mm. The maximum width or width is typically measured at the widest portion of the pessary device substantially perpendicular to the longitudinal axis.

The pessary devices can have any suitable minimum width that is smaller than the maximum width, including, for example, a minimum width from about 40% to about 95% of the maximum width, from about 40% to about 90% of the maximum width, from about 40% to about 85% of the maximum width, from about 40% to about 80% of the maximum width, from about 45% to about 75% of the maximum width, or from about 50% to about 70% of the maximum width, such as, for example, about 45% of the maximum width, about 50% of the maximum width, about 55% of the maximum width, about 60% of the maximum width, about 65% of the maximum width, or about 70% of the maximum width.

The pessary devices can have a minimum width from about 4 mm to about 28 mm, about 5 mm to about 20 mm, about 8 mm to about 20 mm, from about 8 mm to about 18 mm, or from about 8 mm to about 15 mm, such as, for example, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, or about 20 mm, or any other suitable minimum width. The minimum width or diameter is typically measured at the narrowest portion of the pessary device substantially perpendicular to the longitudinal axis.

The maximum width and the minimum width can be separated by any suitable distance, such as, for example, by about 5 mm, about 10 mm, about 15 mm, about 20 mm, about 25 mm, about 30 mm, about 35 mm, about 40 mm, about 45 mm, about 50 mm, or any other suitable distance.

The pessary devices can have any suitable length, such as, for example, a length from about 35 mm to about 60 mm, about 40 mm to about 55 mm, or about 40 mm to about 50 mm, such as, for example, a length about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm. The length is typically measured substantially parallel to the longitudinal axis of the pessary device.

Generally, the pessary device can have a weight of less than about 10 grams, less than about 9 grams, less than about 8 grams, less than about 7 grams, less than about 6 grams, less than about 5 grams, less than about 4 grams, less than about 3 grams, less than about 2 grams, or about 1 gram, including for example, a weight of from about 1 gram to about 7 grams, or from about 2 grams to about 6 grams, or from about 3 grams to about 5 grams.

Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. In certain embodiments, the pessary devices are not formed from absorbent material such as, for example, fibrous material or absorbent foam.

Pessary devices can be formed in any suitable manner, such as, for example, using injection molding or other suitable methods of forming the pessary device.

The pessary device can be covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable width can be used, such as, e.g., from about 0.5 to about 50 microns, such as, e.g., from about 1 to about 30 microns, such as, e.g., from about 10 to about 25 microns. Fiber width can be determined using any suitable means; however, for non-round fibers, width can typically be determined by reference to the width of a fiber with the same cross-sectional area as the non-round fiber.

The overwrap can be made by any number of suitable techniques and can have any suitable basis weight. Suitable techniques include, for example, carding, meltblowing, spunbonding, spunlacing, air laying, and the like. For example, the overwrap can be formed using bonding methods, such as, e.g., thermal, ultrasonic, resin, through-air bonding, hydroentangling, and/or needling. The basis weight of the overwrap can be any suitable weight, such as, e.g., from about 10 to about 60 grams per square meter (gsm), such as, e.g., from about 15 to about 30 gsm. In addition, the overwrap can be hydrophilic or hydrophobic.

The overwrap can be joined to the pessary device by any variety of means. The overwrap can be joined to itself or to the pessary device. For example, one portion of overwrap can be joined to an opposed portion of the overwrap or to the pessary device using any suitable adhesive or heat pressure bonding means. Such adhesive can extend continuously along the length of attachment or it can be applied in a non-continuous fashion at discrete intervals. Heat bonding includes thermally bonding, fusion bonding, or any other suitable means for joining such materials.

The pessary device can include a withdrawal member that can comprise any suitable material, including for example, cotton, cellulose, rayon, polyolefins such as, for example, polyethylene or polypropylene, nylon, silk, polytetrafluoroethylene, wax, or any other suitable materials.

The withdrawal member can be formed by any suitable formation method and in any suitable configuration, such as, e.g., one or more cords, strings, finger covers, ribbons, an extension of a material of the device, or combinations thereof.

The pessary device can be inserted using an applicator that can include an insertion member and a plunger. The insertion member can have an insertion end and a withdrawal end opposite the insertion end. The insertion member also can include a barrel region adapted to contain the pessary device, and a grip region that can, in certain embodiments, be an indentation region provided opposite the insertion end, such as, e.g., proximal to the withdrawal end.

The insertion member and/or plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, and/or any other suitable additives. The insertion member also or alternatively can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

The insertion member can include a grip region, such as, for example, an indentation region. The grip region can have a plurality of three-dimensional surface elements, such as, e.g., projections, rings, ridges, ribs, embossments, depressions, grooves, and/or other gripping structures. The three-dimensional surface elements can be provided in any suitable manner, such as, e.g., by the addition of material, and/or by impressing, such as, e.g., by embossing, or compressing the surfaces. For example, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the applicator into the body. Suitable materials that can provide friction include, for example, abrasive materials, high wet coefficient of friction materials, pressure sensitive adhesives, or any combinations thereof.

The pessary device can be used daily. For example, in certain embodiments, a user can insert the pessary device, wear the pessary device for a suitable wear time, such as, for example, up to 4 hours, up to 5 hours, up to 6 hours, up to 7 hours, up to 8 hours, up to 9 hours, up to 10 hours, up to 11 hours, or up to 12 hours, or more, remove the pessary device, dispose of the pessary device, and insert a new pessary device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An intravaginal pessary device, the device having a longitudinal axis, a top, a mid-section, and a bottom, the device having a sidewall that extends between the top and the bottom, the device being symmetrical about the longitudinal axis, the top, the bottom, and the sidewall forming an outer periphery defining a total area of the device, the device having an interior that is substantially enclosed by the top, the bottom, and the sidewall, the bottom having a first width and the mid-section having a second width, wherein the first width is greater than the second width, the bottom having a first flexibility and the mid-section having a second flexibility, wherein the second flexibility is greater than the first flexibility, and wherein the total length of the pessary is less than 60 mm and the total weight is less than 9 grams, wherein the device is non-expandable.

2. The pessary device of claim 1, wherein the pessary device is in the shape of a teardrop, an apple, a pear, an hourglass, a waisted cylinder, a figure-8, a peanut, a heart, a light bulb, a bottle, or a vase.

3. The pessary device of claim 1, wherein the sidewall is curvilinear.

4. The pessary device of claim 1, wherein the pessary device is formed from a polymeric material.

5. The pessary device of claim 1, wherein the mid-section is concave.

* * * * *